US010349894B2

(12) United States Patent
Shan

(10) Patent No.: US 10,349,894 B2
(45) Date of Patent: Jul. 16, 2019

(54) MOTION ROBUST VITAL SIGNAL MONITORING

(71) Applicant: KONINKLIJKE PHILIPS N. V., Eindhoven (NL)

(72) Inventor: Caifeng Shan, Eindhoven (NL)

(73) Assignee: KONINKLIJKE PHILIPS N. V., Eindhoven (NL)

( * ) Notice: Subject to any disclaimer, the term of this patent is extended or adjusted under 35 U.S.C. 154(b) by 402 days.

(21) Appl. No.: 14/031,451

(22) Filed: Sep. 19, 2013

(65) Prior Publication Data

US 2014/0088433 A1 Mar. 27, 2014

Related U.S. Application Data

(60) Provisional application No. 61/706,173, filed on Sep. 27, 2012.

(30) Foreign Application Priority Data

Sep. 21, 2012 (EP) ..................................... 12185469

(51) Int. Cl.
*A61B 5/00* (2006.01)
*A61B 5/08* (2006.01)
(Continued)

(52) U.S. Cl.
CPC .............. *A61B 5/7207* (2013.01); *A61B 5/00* (2013.01); *A61B 5/0059* (2013.01);
(Continued)

(58) Field of Classification Search
None
See application file for complete search history.

(56) References Cited

U.S. PATENT DOCUMENTS 8,805,019 B2 8/2014 Jeanne
2008/0001735 A1 1/2008 Bao
(Continued)

FOREIGN PATENT DOCUMENTS

EP 0919184 A1 6/1999
WO WO-2011/042844 A1 * 4/2011 ............... G06T 7/20
(Continued)

OTHER PUBLICATIONS

Maarten van den Helder, "Motion Robust Techniques for Camera-Based Monitoring of Respiration", Jul. 2011.*
(Continued)

*Primary Examiner* — Carolyn A Pehlke
*Assistant Examiner* — Marjan Saboktakin

(57) ABSTRACT

The present invention relates to a device and a method for extracting physiological information from remotely detected electromagnetic radiation emitted or reflected by a subject. A data stream derivable from electromagnetic radiation emitted or reflected by a subject is received. The data stream comprises a sequence of signal samples indicative of desired subject motion and of disturbing motion. The signal samples represent at least one region of interest exhibiting an at least partially periodic indicative motion pattern attributable to at least one physiological parameter, and a non-indicative motion region. The sequence of signal samples is processed, comprising deriving a sequence of derivative motion compensated samples at least partially compensated for undesired overall motion; detecting an evaluation parameter representative of motion compensation accuracy; and deriving at least one characteristic signal at least partially indicative of the at least partially periodic indicative motion pattern from the sequence of motion compensated samples, wherein deriving the characteristic signal is performed depending on the detected evaluation parameter.

14 Claims, 6 Drawing Sheets

(51) Int. Cl.

| | |
|---|---|
| ***A61B 5/11*** | (2006.01) |
| ***A61B 5/024*** | (2006.01) |
| ***A61B 5/113*** | (2006.01) |
| ***G06T 7/246*** | (2017.01) |
| ***G06T 7/254*** | (2017.01) |

(52) U.S. Cl.

CPC ............ *A61B 5/0075* (2013.01); *A61B 5/024* (2013.01); *A61B 5/08* (2013.01); *A61B 5/1128* (2013.01); *A61B 5/721* (2013.01); *A61B 5/7278* (2013.01); *G06T 7/246* (2017.01); *G06T 7/248* (2017.01); *G06T 7/254* (2017.01); *A61B 5/113* (2013.01); *A61B 2560/0431* (2013.01); *A61B 2560/0487* (2013.01); *A61B 2576/00* (2013.01); *G06T 2207/10016* (2013.01); *G06T 2207/20224* (2013.01); *G06T 2207/30004* (2013.01); *G06T 2207/30076* (2013.01); *G06T 2207/30104* (2013.01)

(56) References Cited

U.S. PATENT DOCUMENTS

2008/0068458 A1* 3/2008 Carroll ............ G08B 13/19656 348/143
2008/0284908 A1* 11/2008 Chang .................. H04N 7/014 348/452
2009/0028411 A1 1/2009 Pfeuffer
2010/0061596 A1 3/2010 Mostafavi et al.

FOREIGN PATENT DOCUMENTS

WO 2012066454 5/2012
WO 2012140531 A1 10/2012

OTHER PUBLICATIONS

Grimaldi, D., et al.; Photoplethysmography Detection by Smartphone's Videocamera; 2011; IEEE Intl Conf. on Intelligent Data Acquisition and Advanced Computing Systems Technology and Applications; pp. 488-491.

Hulsbusch, M.; Dissertation: Ein bildgestutztes funktionelles Verfahren zur optoelektronischen Erfassung der Hautperfusion; 2008; pp. 1-145.

Sun, Y., et al.; Motion-compensated noncontact imaging photoplethysmography to monitor cardiorespiratory status during exercise; 2011; Journal of Biomedical Optics; 16(7)077010-1-9.

Lowe, D. G.; Distinctive Image Features from Scale-Invariant Keypoints; 2004; International Journal of Computer Vision; 60(2)91-110.

Sahindrakar, P.; Improving Motion Robustness of Contact-less Monitoring of Heart Rate Using Video Analysis; 2011; Technische Universiteit, Dept. of Mathematics and Computer Science; Eindhoven, NL.

Shi, J., et al.; Good Features to Track; 1994; IEEE Computer Society Conference on in Computer Vision and Pattern Recognition; pp. 593-600.

Van Den Helder, M.; Motion robust techniques for camera-based monitoring of respiration; 2011; Technical University of Eindhoven; pp. 1-11.

Verkruysse, W., et al.; Remote plethysmographic imaging using ambient light; 2008; Opt. Express.; 16(26) 21434-21445.

* cited by examiner

MOTION ROBUST VITAL SIGNAL MONITORING

CROSS REFERENCE TO RELATED APPLICATIONS

This application claims the benefit of EP provisional application serial no. 12185469.9 filed Sep. 21, 2012 and U.S. provisional application Ser. No. 61/706,173 filed Sep. 27, 2012, both of which are incorporated herein by reference.

FIELD OF THE INVENTION

The present disclosure relates to a device and a method for extracting physiological information from remotely detected electromagnetic radiation emitted or reflected by a subject, wherein the physiological information is embodied in a data stream comprising a sequence of signal samples indicative of desired subject motion and of disturbing motion. The present disclosure further relates to a computer readable non-transitory medium.

BACKGROUND OF THE INVENTION

US 2010/0061596 A1 discloses a method of determining a similarity with a portion of a physiological motion, the method comprising the steps of:

- obtaining a first image of an object;
- obtaining a second image of the object;
- determining a level of similarity between the first and the second image; and
- correlating the determined level of similarity between the first and second images with a portion of the physiological motion.

The document further discloses several refinements of the method. In particular, the document is directed to patient monitoring, such as monitoring breathing activity of a patient. Vital signal monitoring grows in significance in several fields of application, such as patient monitoring and monitoring sports and fitness activities, for example. Further beneficial applications can be envisaged. Although considerable progress in the field of monitoring performance has been achieved, it is still a challenge to provide for instant signal recognition and signal processing enabling immediate, so-to-say, on-line detection of desired vital signals. This applies in particular to hand-held mobile devices commonly lacking of sufficient computing power and typically exposed to challenging monitoring conditions and constraints.

A further challenge may arise from disturbances and restrictions which have to be taken into account for the detection of the desired signals. As known in the art, detection quality can be improved through applying obtrusive (or: tactile) measurement. For monitoring breathing activity or, in other words, respiration activity, obtrusive measurement devices may comprise belts or sensors which typically have to be attached to a subject's body. Furthermore, referring to remote detection approaches, prior art devices and methods may require markers or similar items which have to be applied to the subject to be observed. These markers can be remotely monitored since they provide sufficient "detectability" and may be considered prominent targets for a detecting device. Still, however, obtrusive measurement, either applied remotely or via tactile measurement devices, is considered unpleasant and uncomfortable by many observed subjects.

Remote unobtrusive measurement typically enables a recording or monitoring of the subject of interest without applying any components or "hardware" to the subject at all. Consequently, since no hardware markers are available, remote unobtrusive detection is widely subjected to disturbances. Recently, even mobile hand-held devices for remote monitoring of vital signals have been envisaged. Mobile hand-held devices are even more susceptible to disturbances since they are typically hand-operated without fixed support. Consequently, huge disturbances attributable to non-indicative device motion with respect to the subject to be monitored have to be expected.

Therefore, it has to be taken into account that the recorded data, such as captured reflective or emitted electromagnetic radiation (e.g., recorded image frames), typically comprises major signal components deriving from overall disturbances. Disturbance-related signal components overlay and affect the desired vital signals basically addressed when monitoring the subject. Overall disturbances may be attributed to changing luminance conditions and disturbing motion components, for example. Disturbing motion may arise from non-indicative motion of the subject itself, or from undesired motion of the detecting or sensing device. In particular with mobile hand-held monitoring devices, overall motion (or: global motion) is considered a huge challenge. Furthermore, particularly addressing respiration detection via remote unobtrusive measurement devices, subject motion-related signals are, so-to-say, attenuated in case the subject of interest is covered (at least partially), for instance, by clothes or even blankets. This applies in particular when sleeping or lying subjects are addressed. Under such conditions, even removal of a blanket for improving detection accuracy would be considered an unpleasant obtrusive measure. After all, vital signal detection becomes even more difficult since amplitudes and/or nominal values of disturbing signal components are expected to be much larger than amplitudes and/or nominal values of desired signal components to be extracted. Potentially the magnitude of difference between the respective components (e.g., global motion vs. respiration motion) can be expected to even comprise several orders.

A possible approach to this challenge may be directed to providing well-prepared and steady ambient conditions when capturing a signal of interest in which the desired vital signal component is embedded. A minimization of potentially occurring disturbing signal components can be achieved in this way. However, such "laboratory" conditions cannot be transferred into everyday field applications and environments since high efforts and much preparation work would be required therefore.

The required preparation work might comprise, for instance, installation and orientation of several defined standard light sources and, moreover, measures for fixation of the subject to be observed and of the monitoring device so as to avoid disturbing motion. It is considered unlikely that these measures are applicable in everyday environments, such as ambulant or clinical patient monitoring, sleep monitoring, or even in lifestyle environments like sporting and fitness monitoring.

SUMMARY OF THE INVENTION

It is an object of the present invention to provide a device and a method for extracting physiological information from remotely detected electromagnetic radiation providing further refinements facilitating obtainment of the desired vital signals with reduced efforts. It would be further advantageous to provide a device and a method adapted for being less susceptible to disturbances, in particular to disturbances arising from global motion artifacts. Furthermore, it would be advantageous to provide for signal detection approaches enabling improved detection accuracy and reliability.

In a first aspect of the present invention a device for extracting physiological information from remotely detected electromagnetic radiation emitted or reflected by a subject is presented, the device comprising:

- an interface for receiving a data stream derivable from electromagnetic radiation emitted or reflected by a subject, the data stream comprising a sequence of signal samples indicative of desired subject motion and of disturbing motion, the signal samples representing at least one region of interest exhibiting an at least partially periodic indicative motion pattern attributable to at least one physiological parameter, and a non-indicative motion region; and
- a processing unit configured for processing the sequence of signal samples, comprising:
  - a stabilizing means configured for deriving a sequence of derivative motion compensated samples at least partially compensated for undesired overall motion;
  - a motion compensation assessment means configured for detecting an evaluation parameter representative of motion compensation accuracy; and
  - an extractor means configured for selectively deriving at least one characteristic signal at least partially indicative of the at least partially periodic indicative motion pattern from the sequence of motion compensated samples, wherein deriving the characteristic signal is performed depending on the detected evaluation parameter.

The present disclosure is based on the insight that, even though motion compensation measures can be applied to the detected signal samples, the resulting "motion compensated" samples can still be heavily affected by non-indicative motion disturbance remainders. In such a case, advantageously, the respective "motion compensated" samples should be excluded from downstream extraction and analyzation measures since the desired vital signals of interest basically cannot be detected at a required accuracy level.

In this way, it can be achieved that heavily motion corrupted "motion compensation" samples cannot be reflected in correspondingly corrupted vital signals obtained through subsequent processing measures. Vital signals are based on the physiological information that is included in the signal samples.

By contrast, alternative approaches are typically directed to assess signal processing accuracy and, consequently, motion compensation accuracy, at the level of the eventually processed and derived vital signals of interest. This can be considered disadvantageous since in this way also heavily distorted samples can pass accuracy assessment and graded as "good" samples, given that they accidentally fall within a defined value range assigned to "good" samples.

Compared with this, the present disclosure provides for a motion compensation quality assessment sub-routine upstream of (or: proceeding) the actual vital signal extraction and analyzation measures. In other words, the accuracy assessment sub-routine can be interposed between motion compensation and signal extraction measures. In this way, stability assessment can be applied to the motion compensated samples prior to further proceeding.

When addressing remote signal detection on the basis of mobile or hand-held detection devices, often huge motion-related disturbances non-indicative of the signals of interest are present in the detected data. In other words, the presence of huge distortions has to be "accepted" and dealt with. Moreover, it has to be "accepted" that in many environments and fields of application, depending on actual monitoring conditions, at least part of the detected signal samples are distorted to such an extent that the desired vital signals basically cannot be derived therefrom. It is considered beneficial in such cases that these heavily corrupted samples are excluded from further processing in case the motion compensation outcome has been evaluated as being insufficient. Consequently, as indicated above, the device of the disclosure is particularly suited for remote signal detection applications intended for operation without obtrusive markers or similar items. In this connection, mobile applications, hand-held devices, or mobile environments in general can be addressed.

In the field of remote vital signal detection, motion compensation is often addressed. For instance, a transitional shift between two or more consecutive samples (or: image frames) can be estimated through adequate imaging processing algorithms. It goes without saying, that also rotational or tilting movement can be addressed through adequate measures. Shift information or motion information can be utilized for compensating the signals for undesired motion so as to "stabilize" the sequence. However, in this connection, it should be noted that the sequence of signal samples may for example comprise a considerable minute motion pattern of interest primarily addressed. Therefore, overall "smoothening" the sequence of image samples by directly transferring commonly known image processing algorithms may rather level the signals and, consequently, remove the desired signal components from the signal samples.

It is therefore considered beneficial to exclude a highly-indicative region, the region of interest, from motion detection measures. It can be achieved in this way that the minute motion pattern of interest is still present (or: preserved) in the sequence of motion compensated samples. It should be further understood in this connection that typically the characteristic signal which is considered indicative of the vital signal of interest is basically derived from the region of interest rather than from the non-indicative motion region which is basically addressed for non-indicative motion detection.

The device of the disclosure is particularly suited for, but not limited to, detecting a subject's respiration rate, respiration rate variability, heart rate or related derivative parameters such as oxygen saturation. Occurrence and expectable characteristics of such vital signals can be readily predicted or assumed to a certain extent (e.g., an assumed range of the respiration rate). Furthermore, for instance, when aiming at an extraction of the subject's present breath rate, it can be assumed that a cycle of breathing in and breathing out is represented by a characteristic repetitive lifting and lowering of the chest portion and/or the abdominal portion of the subject's body. Needless to say, respiration can also be represented by a characteristic motion of a face portion of the subject (e.g., nasal wings or mouth portions). Basically, indicative subject motion can be considered as physiological information since it is representative of the underlying desired vital signals. In general, the term indicative motion pattern may refer to indicative subject motion-related characteristics (such as frequency and/or amplitude) sought in the sequence of signal samples. As used herein, the term sequence may refer to a continuous or discrete series of signal samples.

The data stream may comprise a sequence of frames or, more precisely, a series of image frames. For instance, RGB-images comprising color information can be utilized. However, also frames representing infrared (IR) and red (R) information can form the sequence of frames. The image frames can represent at least a portion of the observed subject and further elements. Typically, a frame may comprise a two-dimensional array of pixels. However, in some embodiments, a frame may comprise a line array, that is, a single line of pixels, for instance.

There exist several embodiments of the stabilizing means, the motion compensation assessment means and the extractor means. In a first, fairly simple embodiment, the stabilizing means, the motion compensation assessment means and the extractor means are commonly embodied by the processing unit which is driven (or: controlled) by respective logic commands (or: program code). Such a processing unit may also comprise suitable input and output interfaces and, furthermore, additional processing means. However, in the alternative, each or at least some of the stabilizing means, the motion compensation assessment means, the extractor means and (if any) further processing means can be embodied by separate processing means which are controlled or controllable by respective logic commands. Hence, each respective processing means can be adapted to its special purpose. Consequently, a distribution of tasks can be applied, where distinct tasks are processed (or: executed) on distinct single processors of a multi-processor processing unit, or wherein image processing-related tasks are executed on an image processor, while other operational tasks are executed on a central processing unit, for example In a further embodiment the stabilizing means further comprises optical stabilization included in the device for extracting physiological information, which stabilizes image samples by varying the optical path to the sensor means. The stabilizing means may be implemented in the lens, e.g. using a floating lens element that is moved orthogonally to the optical axis of the lens, or by moving the sensor means to counteract the movement of the device. In a further embodiment the device includes a movement sensor (e.g. an accelerometer or gyroscope) to detect device motion and to use detected motion to stabilize recorded image samples. The motion compensation assessment may assess the quality of the motion compensation for example by detecting the similarity between motion compensated image samples. Different illustrative embodiments can take the form of entirely hardware embodiments, entirely software embodiments, or of embodiments containing both hardware and software elements. Some embodiments or aspects can be implemented in software or program code. Program code may have the form of application software program code or of firmware program code, for example.

According to another aspect, the processing unit further comprises an analyzing means configured for determining temporal variations in the characteristic signal, the temporal variations being representative of at least one vital signal.

Basically, the characteristic signal can be considered indicative or representative of the at least one physiological parameter and, at least, in a mediate way, of the desired vital signal of interest. This may apply to the subject's respiration rate, respiration rate variability, pulse rate, blood pressure, heart rate, heart rate variability, oxygen saturation (SpO2), perfusion index, or to respective derivates such as a PPG (photo-plethysmography) wave signal that is derived from the pulsation of the arteries, which are all examples of vital signals. Preferably, the desired vital signal is clearly detectable in the at least one characteristic signal. Signal processing methods can be utilized for extracting the desired signal.

As indicated above, since an upstream motion compensation assessment procedure is implemented, and since the characteristic signal is derived under consideration of the detected evaluation parameter, basically "good" signal samples are processed and, consequently, a considerably "clean" characteristic signal can be delivered to the analyzing means. It should be understood that the characteristic signal can still be somewhat distorted due to a variety of disturbances. However, it is emphasized that the characteristic signal derived under consideration of the detected evaluation parameter may have a significantly improved signal-to-noise ratio since heavily distortion affected motion compensated samples are removed from the signal basis upon which the characteristic signal can be determined. As indicated above, vital signal extraction and analyzation is primarily directed to the region of interest in the signal samples and the motion compensated samples, respectively.

According to yet another aspect the evaluation parameter is a flag parameter representative of a state of a set of states indicative of motion compensation accuracy for a given motion compensated sample, or a given set of motion compensated samples. It should be understood in this connection that motion compensation assessment can be directed to the single sample level or to a set of a plurality of samples. It can be envisaged in the latter case that the evaluation parameter is a moving average evaluation parameter spanning over a plurality of motion compensated samples.

In some embodiments, two states can be assigned to the flag-like evaluation parameter. The states may represent "good" motion compensated samples and "bad" motion compensated samples. Typically, good samples can be utilized during further processing measures. By contrast, bad samples can be excluded from further processing measures. For the sake of understanding, the states can also be regarded as color-coded. A green flag may represent a good motion compensated sample. A red flag may represent a bad motion compensated sample. For grading or evaluating the motion compensated samples (or the sets of motion compensated samples), threshold values can be defined. The threshold values can represent motion compensation accuracy-related parameters utilized by the motion compensated assessment means.

According to a further aspect, the flag-like evaluation parameter can be representative of more than two motion compensation accuracy-indicative states. For instance, three different states may form the set of states. By way of example, a "good" (or: green) flag may be assigned to clearly good motion compensated samples. Furthermore, a "bad" (or: red) flag may be assigned to bad motion compensated samples. In order to expand the set of states, an "average" (or: yellow) flag may be assigned to motion compensated signal samples (or: respective sets) which have been evaluated as providing medium motion compensation quality. Of course, even further intermediate states can be envisaged. By providing a set of three states, a border area can be indicated in which the risk of occurrences of bad motion compensated samples is present. It should be understood in this connection that, in one embodiment, yellow flagged (average) samples are still considered to be applicable for further signal processing measures. A set of states providing more than a good state and a bad state enables to draw attention to a transition area between corrupted samples and high-quality samples. In this way, for example, a user can be advised to keep the monitoring device stable so as to keep away from the bad state.

In case even further states form the set of states a user feedback can be even further detailed. For instance, in case four states are utilized, a first state may be assigned to clearly corrupted samples. A second state may be assigned to samples which are still considered inapplicable but providing motion compensation accuracy close to the threshold. A third state can be assigned to samples which are considered to be applicable but also close to the threshold value for motion compensation accuracy. A fourth state may be assigned to samples which are high graded samples comprising a significantly high signal-to-noise ratio.

According to yet an even further aspect, the extractor means, on the basis of the actual evaluation parameter, selectively performs or omits processing the respective motion compensated samples for deriving the at least one characteristic signal. Corrupted samples or sets of samples can be excluded from the vital signal detection in this way. It should be further noted that the evaluation parameter can be a discrete parameter representing discrete values or flags. However, in the alternative, the evaluation parameter can also be defined as a decimal parameter which may represent decimal numbers and, consequently, even further intermediate values enabling to describe motion compensation accuracy with precise figures.

According to still yet another aspect, the stabilizing means is configured for deriving the sequence of derivative motion compensated samples under consideration of at least one portion of the non-indicative motion region in the signal samples.

As indicated above, it is preferred that motion estimation or motion determination which may provide input parameters for motion compensation is not based on the region of interest. In particular, for hand-held or mobile devices, sensor motion (or: camera motion) with respect to the subject of interest can be addressed in this way. It is therefore preferred that the at least one portion of the non-indicative motion region which is utilized for motion compensation represents considerably static elements or objects which may serve as a proper basis for motion estimation.

According to a further aspect of this embodiment, the stabilizing means is further configured for detecting and tracking local features in the least one portion of the non-indicative motion region in the signal samples of the sequence. To this end, in one embodiment, optical flow considerations can be utilized. In this connection, the stabilizing means can make use of Lucas-Kanade-tracking approaches. In the alternative, or in addition, feature-based image registration approaches can be utilized. Furthermore, additionally or alternatively, feature detection approaches can be exploited, such as edge detection, corner detection, and blob detection, respectively. Still, according to an alternative or additional aspect, feature description models can be used for feature tracking and, consequently, for motion estimation. Feature description models may comprise scale-invariant feature transformation (SIFT), speed-up robust feature detection (SURF), gradient location and orientation histogram image description (GLOH), histogram of oriented gradients feature description (HOG), local energy based shape histogram image description (LESH), etc. Again, it is worth noting that the afore-mentioned approaches are preferably applied to the at least one portion of the non-indicative motion region since in this way undesired exaggerated motion compensation within the region of interest and, therefore, adversely affecting the desired indicative motion pattern can be avoided. It is worth noting in this connection that indeed motion compensation measures can be applied to the region of interest. However, given that motion detection is performed outside the region of interest, rather global motion compensation instead of indicative motion compensation is applied to the region of interest. Typically, the subtle motion pattern of interest can be preserved in this way.

According to another aspect of the device, the motion compensation assessment means is configured for detecting a similarity between motion compensated samples under consideration of at least one portion of the non-indicative motion region in the motion compensated samples.

Also in this connection it is a preferred aspect in one embodiment that motion compensation assessment is not performed in the region of interest. By way of example, motion compensation assessment can be based on a reference sample which may serve as a reference to which an actual motion compensated sample is compared. The reference sample can be a fixed reference sample, for instance, an initial sample out of a sequence of samples. In the alternative, the reference sample can be a moving reference sample, wherein a defined (temporal) distance or relation between the reference sample and the actual motion compensated sample is kept when a series of motion compensated samples is processed for motion compensation assessment measures. The reference sample and the actual motion compensated sample can be consecutive samples or samples that are spaced in the sequence of motion compensated samples, that is, intervening samples may be present.

As indicated above, the evaluation parameter can be based on processing a single motion compensated sample (and a respective reference sample). In the alternative, the evaluation parameter can represent motion compensation accuracy of a set of motion compensated samples with respect to respective reference samples. In this way, the evaluation parameter may represent a moving average value for motion compensation accuracy.

As used herein, the term non-indicative motion region may basically refer to a portion of both the (input) signal samples and the motion compensated samples which is not occupied by the region of interest. Consequently, the terms region of interest and non-indicative motion region can be used in connection with both the initially motion-affected signal samples and the motion compensated samples. The term "at least a portion of the non-indicative motion" region may refer to a respective subset.

According to a further aspect of the above embodiment, the motion compensation assessment means is further configured for applying an absolute difference processing algorithm to the at least one portion of the non-indicative motion region in a respective motion compensated sample with respect to a reference sample. By way of example, the sum of absolute differences (SAD) approach can be chosen so as to detect a similarity between actual motion compensated samples and respective reference samples. A remaining difference between respective processed samples may be reflected in the evaluation parameter.

According to another aspect, the motion compensation assessment means is configured for detecting feature correspondences in at least one portion of the non-indicative motion region in a respective motion compensated sample and in a reference sample. It is worth noting again that basically feature detection is not directed to the region of interest but rather to the non-indicative motion region. By way of example, a number of detected feature correspondences can indicate a degree of motion compensation accuracy and, consequently, be reflected in the detected evaluation parameter. As already indicated above, the reference sample can be formed by a fixed reference sample or by a moving reference sample keeping a defined relation (distance or gap) to a currently processed motion compensated sample.

According to yet another preferred aspect, the motion compensation assessment means is further configured for detecting the evaluation parameter under consideration of a plurality of motion compensation assessment indicators. By way of example, motion compensation can make use of both absolute difference processing and feature correspondences detecting applied to the motion compensated samples under consideration of respective reference samples. In this way, at least two motion compensation accuracy-related indicators can be obtained. It can be therefore defined that certain conditions have to be met so as to selectively perform or omit further processing of the respective motion compensated sample (or the respective set of samples) for deriving the at least one characteristic signal. In this connection, two respective thresholds can be defined such that further processing of the motion compensated samples is performed merely in case both indicators are above (or, respectively, below) the thresholds differentiating the motion compensated samples into good ones and bad ones. However in the alternative, the device can be configured such that further processing of the respective motion compensated samples is conducted in the event that at least one indicator exceeds (or comes below) the respective threshold.

According to yet a further aspect, the device further comprises a signal generation unit configured for generating a noticeable output signal depending on the actual evaluation parameter, wherein the output signal preferably indicates a state of a set of states indicative of motion compensation accuracy. In this way, the device can further provide user feedback and advice directed to further enhance motion compensation accuracy and, consequently, signal detection accuracy. As used herein, the term noticeable output signal may relate to an output signal which is clearly noticeable for a user of the device. The output signal may comprise, for example, sound signals, speech, visible signals, indicating lights, displayed information, tactile signals, and suitable combinations thereof. The output signal or the output signals may represent the actual evaluation parameter. Therefore, for instance, the signal generation unit can be configured for displaying or transmitting red light (representing bad samples), green light (representing green samples) and, if any, yellow light (representing average samples). Noticing a red indicating light, the user may be advised to keep the monitoring device stable since currently no vital signal processing can be conducted due to motion-related disturbances. Noticing a green indicating light, the user can be informed that the device is working well and that signal detection accuracy clearly exceeds a threshold level. Noticing a yellow indicating light, the user can be informed that currently signal processing can be conducted but that signal process accuracy (or, more precisely, motion compensation accuracy) is close to the threshold level. In this way, the user can be prompted to reduce adverse motion influences.

According to yet another aspect, the device further comprises a sensor means, particularly a hand-held sensor means, configured for capturing electromagnetic radiation within at least one particular wavelength range selected from the group consisting of visible light, infrared light, and ultraviolet radiation, the sensor means being connectable to the interface. By way of example, the sensor means can be embodied by a camera. For instance, the sensor means can be embodied by a mobile device having an integrated camera or an attachment camera, such as a personal digital assistant, a mobile phone, a mobile computer, a tablet computer, etc. However, in the alternative, the sensor means also can be embodied by a laser scanner device. Furthermore, the sensor means can be part of a mobile medical monitoring device.

According to another aspect, the device may further comprise at least one source of illumination configured for emitting radiation. In the alternative, the device can also make use of external or even ambient radiation sources. According to another aspect, the analyzing means is further configured for applying an integral transformation, for example a Fourier transformation to the at least one characteristic signal, thereby obtaining frequency information attributable to the desired indicative subject motion pattern representative of the vital signal.

In a further aspect of the present invention a device for extracting physiological information from remotely detected electromagnetic radiation emitted or reflected by a subject is presented, the device comprising:

- an interface for receiving a data stream derivable from electromagnetic radiation emitted or reflected by a subject; and
- a processing unit configured for processing the sequence of signal samples, comprising:
  - a stabilizer configured for deriving a sequence of derivative motion compensated samples;
  - a motion compensation assessment module configured for detecting an evaluation parameter representative of motion compensation accuracy;
  - an extractor configured for selectively deriving at least one characteristic signal at least partially indicative of an at least partially periodic indicative pattern; and
  - an analyzer configured for determining temporal variations in the characteristic signal, the temporal variations being representative of at least one vital signal;

wherein the data stream comprises a sequence of signal samples including physiological information and indicative of disturbing motion, the signal samples representing at least one region of interest exhibiting the at least partially periodic indicative pattern attributable to at least one physiological parameter, and a non-indicative motion region;

wherein the derivative motion compensated samples are at least partially compensated for undesired overall motion;

wherein the at least partially periodic indicative pattern is derived from the sequence of motion compensated samples; and wherein deriving the characteristic signal is performed depending on the detected evaluation parameter.

In a further aspect of the present disclosure, a method for extracting physiological information from remotely detected electromagnetic radiation emitted or reflected by a subject is presented, the method comprising the steps of:

- receiving a data stream derivable from electromagnetic radiation emitted or reflected by a subject, the data stream comprising a sequence of signal samples indicative of desired subject motion and of disturbing motion, the signal samples representing at least one region of interest exhibiting an at least partially periodic indicative motion pattern attributable to at least one physiological parameter, and a non-indicative motion region; and
- processing the sequence of signal samples, comprising:
- deriving a sequence of derivative motion compensated samples at least partially compensated for undesired overall motion;
- detecting an evaluation parameter representative of motion compensation accuracy; and deriving at least one characteristic signal at least partially indicative of the at least partially periodic indicative motion pattern from the sequence of motion compensated samples, wherein deriving the characteristic signal is performed depending on the detected evaluation parameter.

Advantageously, the method can be carried out utilizing the device for extracting physiological information of the present disclosure.

According to an embodiment the method further comprises the steps of:

on the basis of the actual evaluation parameter, selectively performing or omitting processing the respective motion compensated samples for deriving the at least one characteristic signal; and determining temporal variations in the characteristic signal, the temporal variations being representative of at least one vital signal.

In a further aspect of the present invention, a method for extracting physiological information from remotely detected electromagnetic radiation emitted or reflected by a subject is presented, the method comprising the steps of:

receiving a data stream derivable from electromagnetic radiation emitted or reflected by a subject, the data stream comprising a sequence of signal samples including physiological information and indicative of disturbing motion, the signal samples representing at least one region of interest exhibiting an at least partially periodic indicative pattern attributable to at least one physiological parameter, and a non-indicative motion region; and processing the sequence of signal samples, comprising:

deriving a sequence of derivative motion compensated samples at least partially compensated for undesired overall motion;

detecting an evaluation parameter representative of motion compensation accuracy; and deriving at least one characteristic signal at least partially indicative of the at least partially periodic indicative pattern from the sequence of motion compensated samples, wherein deriving the characteristic signal is performed depending on the detected evaluation parameter.

In yet another aspect of the present disclosure, there is provided a computer program which comprises program code means for causing a computer to carry out the steps of the processing method when said computer program is carried out on the computer.

As used herein, the term computer stands for a large variety of processing devices. In other words, also mobile devices having a considerable computing capacity can be referred to as computing device, even though they provide less processing power resources than standard desktop computers. Furthermore, the term a "computer" may also refer to a distributed computing system which may involve or make use of computing capacity provided in a cloud environment.

Preferred embodiments of the disclosure are defined in the dependent claims. It shall be understood that the claimed methods and the claimed computer program can have similar preferred embodiments as the claimed device and as defined in the dependent device claims.

BRIEF DESCRIPTION OF THE DRAWINGS

These and other aspects of the disclosure will be apparent from and elucidated with reference to the embodiments described hereinafter. In the following drawings.

DETAILED DESCRIPTION OF THE INVENTION

Figure 1:
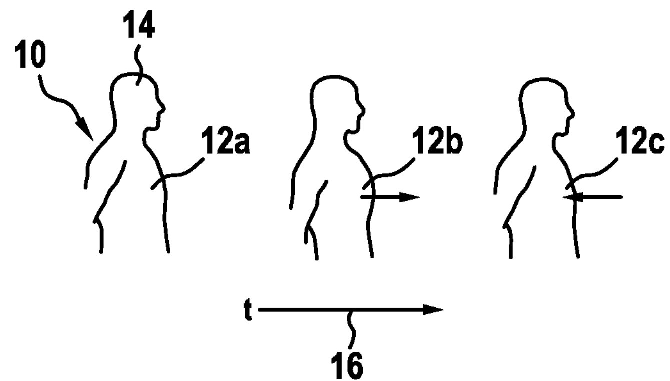
FIG. 1 shows a schematic illustration of subject motion indicative of an exemplary vital signal.

FIG. 1 shows a schematic illustration of a subject 10 which experiences motion indicative of a signal of interest. The subject 10 undergoes a characteristic motion of an indicative portion 12 due to respiration. When breathing, expansion and contraction of the lungs or the diaphragm causes slight motion of characteristic portions in living beings, in particular lifting and lowering of the chest. Also abdominal breathing can cause characteristic motion of respective parts of the subject's body. At least partially periodic motion patterns induced by various physiological processes can occurred in many living beings, particularly in humans or animals. Over time, as indicated by an arrow 16, the indicative portion 12 is moved between a contracted position, indicated by reference numerals 12*a*, 12*c*, and an extracted position, indicated by reference numerals 12*b*. By way of the example, based on this motion pattern (herein also referred to as physiological information 56, refer to FIG. 2) the respiration rate or respiration rate variability can be assessed. While the indicative portion 12 is pulsating over time, a non-indicative portion 14 remains substantially motionless (in terms of the desired motion pattern). Certainly, also the non-indicative portion 14 can undergo diverse motion over time. However, this motion typically does not correspond to the periodic pulsation of the indicative portion.

In another example the characteristic movement of the indicative portion 12 results from pulsating arteries in the skin of the subject. The pulsating arteries cause a minute motion of the surface texture due to the pumping of the heart.

Figure 2:
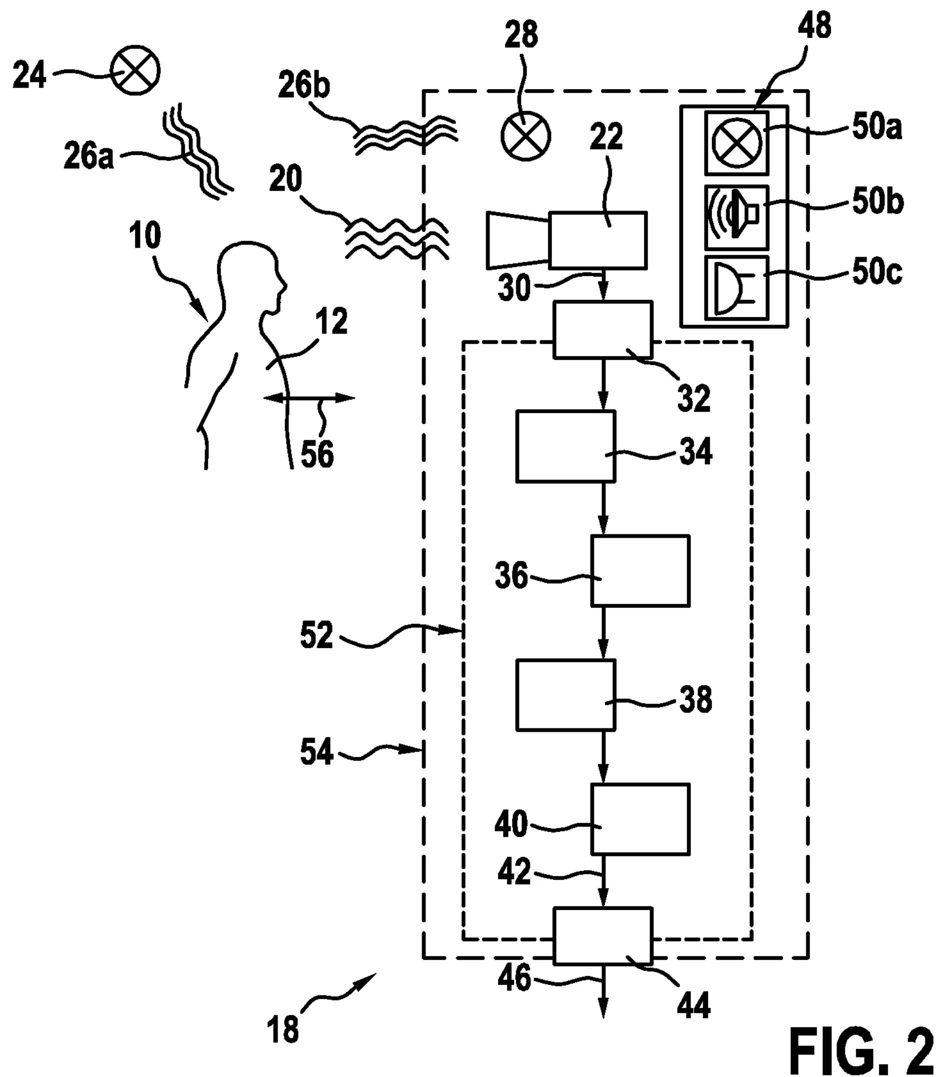
FIG. 2 shows a schematic illustration of a general layout of a device in which the present invention can be used.

Now referring to FIG. 2, a device for extracting information is illustrated and denoted by a reference numeral 18. The device 18 is particularly suited for detecting motion of an indicative portion 12 of the subject 10 which is related to physiological information, refer also to the arrow 56 in this regard. The device 18 can be utilized for recording image frames representing the subject 10. The image frames can be derived from electromagnetic radiation 20 emitted or reflected by the subject 10. For extracting information from the recorded data, e.g. from a sequence of image frames, a defined part or portion of the subject 10 can be observed by a sensor means 22. The sensor means 22 can be embodied, for instance, by a camera adapted to capture information belonging to at least one respective component of the electromagnetic radiation 20. The sensor means 22 may comprise an array of single sensor elements. For instance, the sensor means 22 can make use of a line array or of a matrix array of single sensors, such as charge-coupled devices (CCD-sensors). Still, however, also alternative sensor types can be utilized. It is worth noting that the device 18 also can be primarily configured for processing input signals, namely an input data stream, already recorded in advance, and, in the meantime, stored or buffered. In this connection, recording can be performed by a separate remote sensor means.

As indicated above, the electromagnetic radiation 20 can contain a continuous or characteristic signal which is considered to be highly indicative of at least one at least partially periodic vital signal but, on the other hand, typically massively distorted by overall disturbances such as global motion and varying illumination conditions. This applies in particular when the device 18 or, at least, the sensor means 22 is arranged as a remote mobile device. In some embodiments, the device 18 can make use of defined illumination sources or, in general, radiation sources 24, 28. Illumination source 24 can be considered an ambient separate source of radiation. Illumination source 28 can be considered an internal controllable source of radiation. The radiation sources 24, 28 basically emit incident radiation 26*a*, 26*b* striking the subject 10. Typically, the incident radiation 26*a*, 26*b* is at least partially reflected by the subject 10. Furthermore, in particular for embodiments making use of infrared (e.g., near-infrared or deep-infrared) radiation, also the subject 10 may emit (or: generate) radiation portions, such as thermal radiation.

Known methods for obtaining vital signals such as respiration-related signals comprise tactile respiration rate monitoring and remote respiration rate monitoring relying on markers applied to the subject of the interest. To this end, however, obtrusive monitoring is required. As indicated above, an alternative approach is directed to remote unobtrusive measuring utilizing specific image processing methods.

The sensor means 22 can be configured for delivering a data stream 30 to an interface 32. Needless to say, also a buffer means could be interposed between the sensor means 22 and the interface 32. Downstream of the interface 32 a stabilizing means 34 may be provided. Basically, the stabilizing means 34 can be configured for applying motion compensation measures to the data stream 30. In this way, a sequence of signal samples embodied in the data stream 30 can be transformed into a sequence of derivative motion compensated samples. At this level, motion compensation is directed to overall motion which can be caused by relative motion between the subject 10 and the sensor means 22. As used herein, overall motion primarily relates to motion of the sensor means 22 or, in general, motion of the device 18 comprising the sensor means 22. A monitoring environment typically comprises at least a part of the subject 10, peripheral elements such as walls, furniture or even non-indicative portions of the subject 10, and the sensor means 22 directed to the subject 10. Among these elements, undesired relative motion can occur. In particular, for mobile applications making use of hand-held portable devices 18 or, at least, sensor means 22, the detected sequence of signal samples can be heavily affected by shaking or blurring effects caused on the end of the sensor means 22. Typically, these undesired disturbances exceed the desired patterns in magnitude.

These desired patterns may for example be motion patterns and for example result from a desired subject movement such as a respiratory induced movement of the chest. The characteristic movement of the indicative portion 12 may for example also result from pulsating arteries in the skin of the subject causing minute motion patterns. The radiation sources 24, 28 (see FIG. 2) emit incident radiation 26*a*, 26*b* striking the subject 10. By travelling through the skin the radiation undergoes an amount of absorption that depends on the length of the path that the radiation travels through the skin and the absorption coefficient of the substance (e.g. blood, tissue). As the arteries are pulsating their diameter changes over time with the blood volume pulse causing in the region of interest the intensity of the electromagnetic radiation emitted or reflected by the subject to change with the frequency of the heart rate.

In another example the desired patterns relate to patterns in frequency and intensity of reflected or emitted light such as skin color variations. The pulsation of arterial blood causes changes in light absorption. Those changes form a PPG (photo-plethysmography) signal (also called, among other, a pleth wave). It is based on the principle that temporal variations in blood volume in the skin lead to variations in light absorptions by the skin. Such variations can be registered by a video camera that takes images of a skin area, e.g. the face, while processing calculates the pixel average over a selected region of interest (typically part of the cheek). By looking at periodic variations of this average signal, the heart beat rate and respiratory rate can be extracted. A method to measure skin color variations, called Photo-Plethysmographic imaging (PPG), is described in Wim Verkruysse, Lars O. Svaasand, and J. Stuart Nelson, "Remote plethysmographic imaging using ambient light", Optics Express, Vol. 16, No. 26, December 2008.

As indicated above, primary motion compensation measures may result in signal samples which may still contain motion-related disturbances. Therefore, depending on present motion influences affecting the signal samples, in some cases also motion compensated samples can still be heavily distorted and therefore not applicable for further processing directed to the extraction of the signal of interest. The present embodiment basically tackles this issue.

The sequence of motion compensated samples can be delivered to a motion compensation assessment means 36. The motion compensation assessment means 36 can be configured for detecting an evaluation parameter representative of motion compensation accuracy. For instance, the motion compensation assessment means 36 can be adapted for determining remaining motion-related distortions in the motion compensated signal samples. In this way, an evaluation parameter can be obtained which is representative of current motion compensation accuracy. The evaluation parameter can be a quality-related parameter. The evaluation parameter can be represented by a value on a scale having a certain range and, furthermore, a threshold value can be defined in this range for determining sufficient motion compensation accuracy and non-sufficient motion compensation accuracy. Consequently, respective motion compensation samples can be flagged so as to indicate whether they are considered applicable for further signal processing measures or still distorted in such a way that no further processing measures on the basis of these samples are recommended.

Consequently, these samples can be excluded from further processing. In some embodiments, the evaluation parameter also can be configured as a flag parameter, wherein a flag can be assigned to signal samples (or respective sets of signal samples), wherein the flag may represent a state of a set of distinct states. The group or set of states may comprise at least one of a bad (or: red) state to be assigned to bad samples and a good (or: green) state to be assigned to good samples. As indicated above, further intermediate stages can be considered.

The device 18 may further comprise an extractor means 38 configured for selectively deriving at least one characteristic signal at least partially indicative of the at least partially periodic indicative pattern from the sequence of motion compensated samples delivered thereto. This periodic indicative pattern may be a motion pattern resulting from a desired subject movement such as for example a respiratory induced movement of the chest or a pattern in frequency and intensity of the reflected or emitted light caused by changes in light absorption of the skin resulting from the pulsation of arterial blood in the skin.

It is preferred that the extractor means 38 is configured for deriving the characteristic signal under consideration on the detected evaluation parameter. In this way, "bad" motion compensated samples can be excluded from further processing. This may apply to a single bad motion compensated sample or to a set of a plurality of bad motion compensated samples. In this way, signal derivation accuracy can be improved since distortions attributable to insufficient motion compensation accuracy can be prevented, at least to a certain extent. It should be noted in this connection, that the sample pool or basis for the derivation of the characteristic signal can be reduced or thinned out in this way. Consequently, in particular when a set comprising a large quantity of motion compensated samples is excluded from further processing, the at least one vital signal eventually cannot be determined for the respective period of time. However, it is considered advantageous to skip the characteristic signal derivation and the vital signal determination based thereon for corrupted (bad) motion compensated samples, compared to processing also corrupted samples without any reflection or consideration of the potential outcome in respect of the desired vital signal of interest.

It should be further noted that, given that only single or only a few of corrupted motion compensated samples are excluded from further processing, in some embodiments the characteristic signal still can be derived and established in a sufficient manner such that eventually the vital signal of interest can be extracted therefrom without considerable interrupt. This may be the case in particular in environments wherein a sample rate or frame rate in the input sequence is sufficiently high in comparison to a frequency, if any, of the vital signal of interest.

The device 18 may further comprise an analyzing means 40 configured for determining temporal variations of the characteristic signal. In particular, the analyzing means 40 can be adapted for seeking for dominant frequencies attributable to the vital signal of interest. Hence, the analyzing means 40 can make use of several signal processing approaches. For instance, the analyzing means 40 can be configured for applying, among other algorithms, a Fourier transformation or a similar integral transformation to the characteristic signal so as to obtain frequency values or even a frequency domain representation of the enhanced characteristic signal.

Eventually, a processed data stream 42 can be generated. The processed data stream 42 can be delivered to an interface 44. Consequently, via the interface 44, output data 46 can be made available to further analysis and/or for display measures. The (input) interface 32 and the (output) interface 44 can be embodied by the same (hardware) interface elements. The stabilizing means 34, the motion compensation assessment means 36, the extractor means 38 and (if any) the analyzing means 40 or even further processing means can be embodied by a common processing unit 52. Also the interfaces 32, 44 can be connected thereto in a common processing device accommodating the respective subcomponents. By way for example, the processing unit 52 can be embodied by a personal computer or a mobile computing device.

Furthermore, the device 18 can comprise a signal generation unit 48 which can be configured for generating an output signal which is noticeable to a user of the device 18. It is preferred that the output signal is generated under consideration of the actual evaluation parameter detected by the motion compensation assessment means 36. In other words, in some embodiments, the motion compensation assessment means 36 can be utilized for "triggering" the signal generation unit 48. The signal generation unit 48 can indicate the actual evaluation parameter to a user of the device 18. As mentioned above, the evaluation parameter can be detected under consideration of a single sample or, in the alternative, under consideration of a set of samples. Consequently, the signal generation unit 48 can be also adapted for representing a mean evaluation parameter which may be a moving average evaluation parameter spanning over a plurality of samples. The signal generation unit 48 can make use of a single or a plurality of indicator source means 50. In this connection, the signal generation unit 48 shown in FIG. 2 comprises an exemplary, but non-limiting, set of indicator sources 50*a*, 50*b*, 50*c*. Indicator source 50*a* can be embodied by a visual indicator source or light indicator source. For instance, the indicator source 50*a* can comprise one or more light sources, such as light emitting diodes (LED). Given that the evaluation parameter is representative of several distinct states indicative of motion compensation accuracy, each of the single light sources of the indicator source 50*a* may represent a respective color. For instance, at least a red and at least a green LED may be utilized. In another embodiment, the indicator source 50*a* comprises a source of red light, a source of yellow light, and a source of green light. Needless to say, the indicator source 50*a* can also be configured for cooperating with filter means such that different indicator lights can be generated under utilization of a single light source. In some embodiments, the visible indicator source 50*a* can make use of a display means. In this connection, LCD displays, LED displays and similar display types can be envisaged. A display may present color information and/or textual information.

Additionally, or in the alternative, the signal generation unit 48 also can make use of a sound indicator source 50*b*. The sound indicator source 50*b* can comprise at least one sound generator, for instance, a loudspeaker. In some embodiments, the sound indicator source 50*b* can be configured for presenting a speech message. However, in the alternative, also a single tone or a tone sequence can be generated by the sound indicator source 50*b*.

According to another alternative embodiment, the signal generation unit 48 can further comprise a tactile indicator source 50*c*. By way of example, the tactile indicator source 50*c* can be embodied by a buzzer or a vibration element. In this way, a subtle signal can be directed to the user of the device 18. Each or at least some of the indicator sources 50*a*, 50*b*, 50*c* can be utilized for providing feedback to the user. The feedback can be generated depending on the current evaluation parameter detected by the motion compensation assessment means. Dependent on the current motion compensation accuracy state, the user can be assured that motion compensation measures are currently considered sufficient for enabling a proper vital signal extraction. However, in the alternative, the user feedback may also indicate that motion compensation measures are currently insufficient such that the desired vital signal extraction is currently not enabled. Furthermore, the user can be advised to keep the device 18 or, at least, the sensor means 22 stable so as to reduce overall motion influences. Needless to say, further feedback messages can be directed to the user. In some embodiments, also the signal generation unit 48 can be accommodated or connected to the processing unit 52.

In case also the sensor means 22 is jointly connected to the processing unit 52, a common housing may accommodate the respective components. In this connection, an overall system boundary is indicated by a reference numeral 54. Reference numeral 54 may also refer to a common housing for the device 18. If such an integrated approach is intended, the device 18 can be embodied by a mobile device such as a smartphone, a tablet computing device or a mobile health monitoring device. These devices can make use of an integrated sensor means (camera) 22 or, at least, being connectable to a separate sensor means (camera) 22. In another exemplary configuration, the device 18 is a stationary device while at least the sensor means 22 is portable. The sensor means 22 can be coupled to a stationary processing unit 52 via suitable cable connections or wireless connections.

Figure 3:
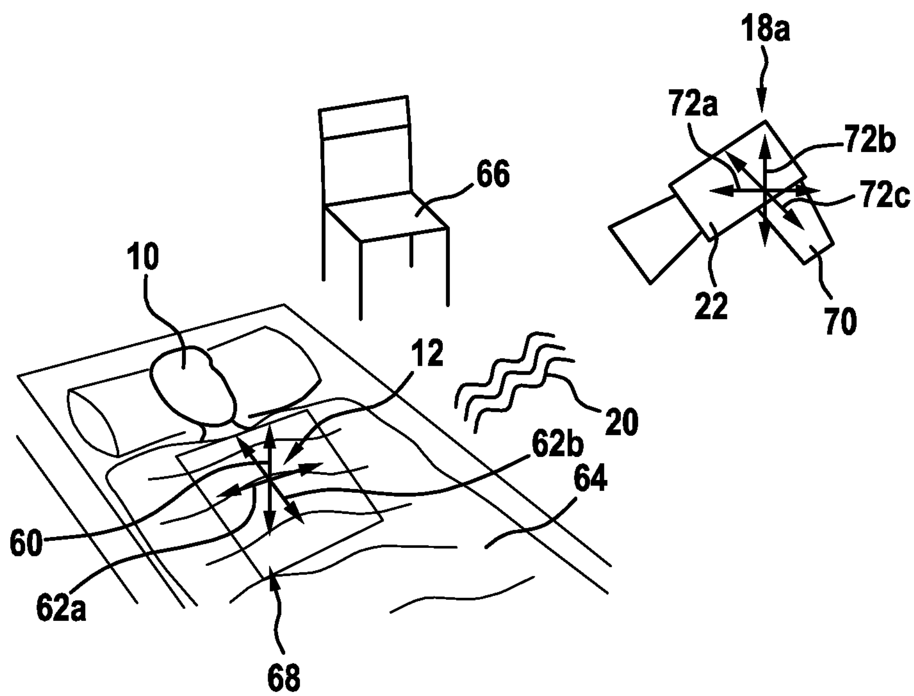
FIG. 3 shows a schematic illustration of an arrangement including a subject to be monitored.

With reference to FIG. 3, a common environment in which unobtrusive vital signal monitoring is performed is presented. The subject 10, e.g. a patient staying in bed, is resting on a support. The subject's 10 head which is attributable to the non-indicative portion 14 (FIG. 1) is exposed and pillowed, while the indicative portion 12, e.g., the chest, is covered by a blanket 64. Thus, the desired signal caused by a motion of the indicative portion 12 is attenuated or hidden. Therefore, obtrusive signal detection is considerably difficult. This applies in particular when a portable mobile monitoring device 18*a* is utilized. The monitoring device 18*a* can comprise a handle 70 a user may grab for holding and orientating the device 18*a*. The device 18*a*, in particular the sensor means 22, can be positioned and orientated such that the indicative portion 12 undergoing the indicative motion pattern can be observed. In this connection, an exemplary region of interest 68 representing the chest portion of the subject 10 is indicated by a quadrangular box. In FIG. 3, an axis 60 indicates an expected direction of the periodic motion pattern of interest. Periodic subject motion along this axis 60 can represent the desired physiological information 56 (FIG. 2). By contrast, potential subject motion in other directions, refer to reference numerals 62*a*, 62*b*, is considered to be not indicative and therefore not of particular interest. The monitoring environment shown in FIG. 3 may further comprise stationary objects, refer to reference numeral 66. Stationary objects 66 may serve as reference objects which may be utilized for motion compensation. Consequently, also the stationary object 66 (e.g., a chair) may be present in the field of view of the sensor means 22. For mobile or portable applications, the sensor means 22 may undergo positional changes and orientation changes when observing the subject 10. Typically, motion of the sensor means 22 may comprise motion along and around several axes, refer to reference numerals 72*a*, 72*b*, 72*c*.

Figure 4:
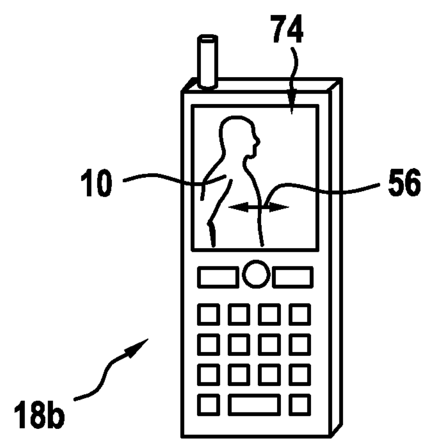
FIG. 4 shows an exemplary simplified illustration of a mobile device in which the present invention can be used.

FIG. 4 illustrates an alternative embodiment including a mobile device 18*b*. Since mobile devices such as mobile phones, tablet computers and notebooks are readily available and, moreover, often include adequate cameras, suitable control algorithms can be implemented so as to control these devices in vital signal monitoring applications. The device 18*b* may comprise a display 74 for representing an indicative portion 12 (represented by the region of interest 68) of the subject 10 exhibiting the desired motion pattern which is attributable to the physiological information 56 of interest. A user may therefore target the subject 10 under consideration of a present representation of the subject 10 in the display 74. Consequently, instant signal detection on a remote basis can be simplified. Needless to say, the device 18*b* can also comprise the signal generation unit 48 (FIG. 2) and at least one of the indicator sources 50*a*, 50*b*, 50*c*. To this end, available implemented signal sources can be utilized.

Figure 5:
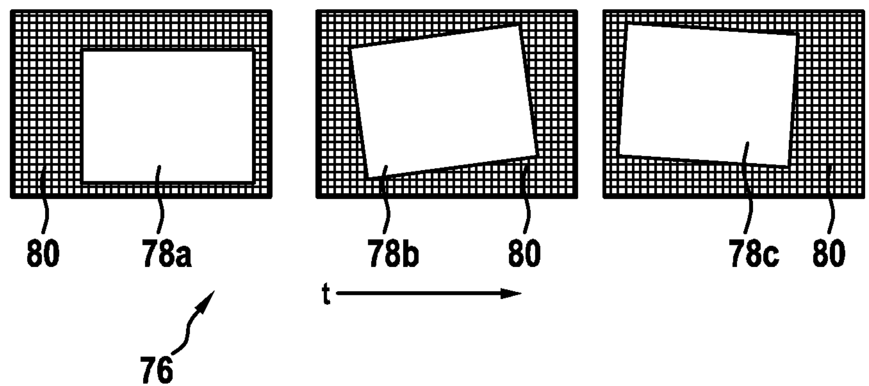
FIG. 5 shows a simplified exemplary sequence of signal samples which are subjected to overall motion.

FIG. 5 illustrates a sequence 76 of signal samples 78*a*, 78*b*, 78*c*. For illustrative purposes, also a spatial reference 80 is indicated. The sequence 76 may comprise a series of signal samples 78*a*, 78*b*, 78*c*. Since motion-related disturbances are to be expected, typically a field of view covered by each of the signal samples 78*a*, 78*b*, 78*c* may vary over the series of samples. Since these deviations are considered to exceed the desired indicative motion pattern in terms of absolute values and amplitudes, motion compensation is crucial for further processing and signal extraction. As already set out above, a sequence of motion compensated samples 106 can be derived from the (original) sequence 76 through motion compensation measures.

Figure 6:
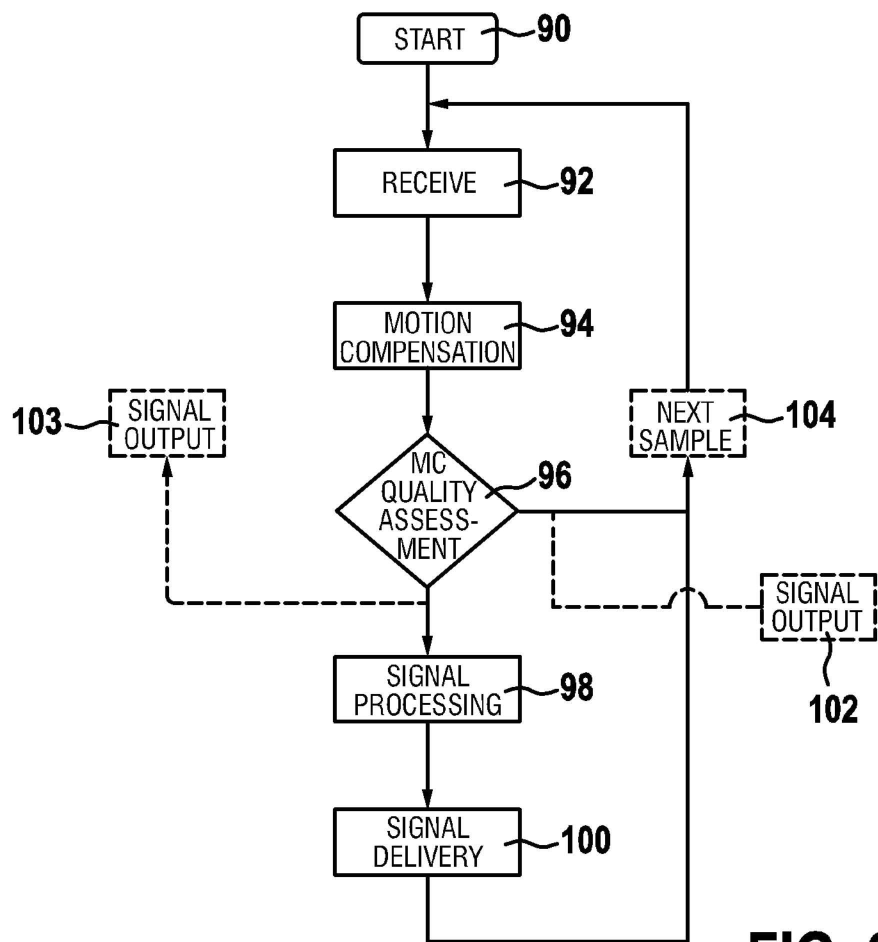
FIG. 6 illustrates a simplified block diagram representing several steps of an embodiment of a method in accordance with the disclosure.

FIG. 6 illustrates a simplified exemplary flow chart diagram representing a method in accordance with an embodiment of the disclosure. The flow chart basically describes a vital signal extraction process which can be applied to signal samples 78*a*, 78*b*, 78*c* in a sequence 76. Initially, the process may be started or triggered at operation 90. At operation 92, a to-be-processed signal sample (e.g., an image frame) is received. As already indicated above, signal processing can be directed to single samples (out of a sequence) or to a set of samples. It should be understood in this connection that the process depicted in FIG. 6 can be understood as a "moving" process consecutively processing consecutive entities in a series (or: sequence) of signal samples.

Subsequently, motion compensation processing (reference numeral 94) can be applied to the to-be-processed sample. Basically, a motion compensated sample can be obtained in this way. A motion compensation accuracy assessment subroutine (process 96) may follow. The motion compensation accuracy assessment subroutine can determine a current motion compensation accuracy level. In this way, an evaluation parameter can be determined which can be considered a motion compensation accuracy indicator value. Depending on whether the indicator value exceeds (or comes below) a defined threshold, it can be decided whether or not the currently assessed motion compensated sample (or the currently assessed set of motion compensated samples) is to be considered during subsequent signal extraction and processing operations. In case a desired accuracy level is found to be met by the respective motion compensated samples, the process may proceed with operation 98 in which signal processing, for instance, respiration rate processing is conducted. In this way, the vital signals of interest can be extracted. Vital signal extraction may comprise a derivation of characteristic signals from the sequence of approved proper motion compensated signal samples. Further signal processing algorithms may be involved. Subsequently, in a delivery operation 100, the vital signals of interest can be made available for display measures, for data storage, and for further data processing.

In case it is found in the motion compensation accuracy assessment operation 96 that a desired accuracy level is not met by the processed motion compensated sample, the respective sample can be excluded from further processing, that is, for instance, from the operations 98 and 100. In other words, the operations 98 and 100 can be bypassed. Instead, an alternative operation 102 may follow in which an output signal can be generated and presented to a user pointing to that situation. For instance, the user can be advised to reduce adverse motion influences by keeping the monitoring device stable. Consequently, an operation 104 may follow in which a next to-be-processed signal sample can be chosen.

It is worth mentioning in this connection that also in the event that the motion compensated signals are found to meet the desired accuracy level, a respective output signal can be generated and presented to the user, refer to the dashed line connected to output signal generation operation 103. Regardless of the outcome of the motion compensation accuracy assessment subroutine 96, eventually the operation 104 may follow in which the next to-be-processed signal sample can be chosen. Consequently, a plurality of signal samples in a sequence can be processed.

Figure 7A:
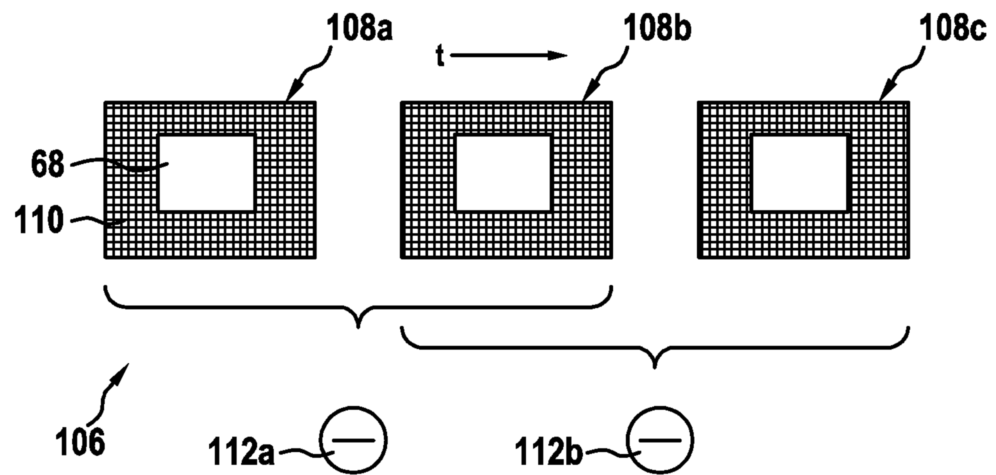
FIG. 7*a* illustrates an exemplary motion compensation accuracy assessment approach.
Figure 7B:
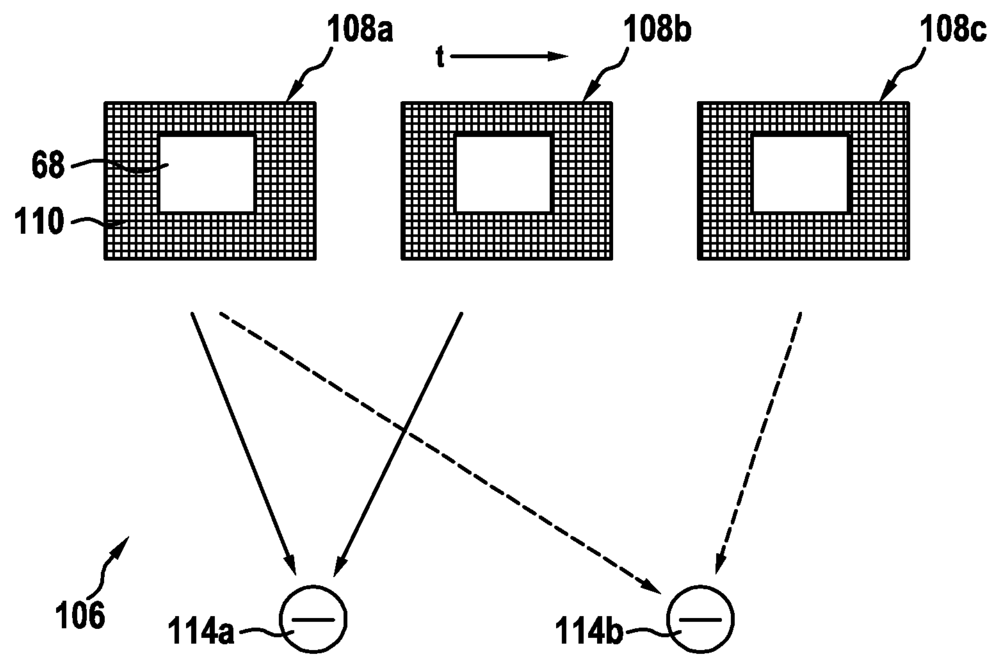
FIG. 7*b* illustrates an alternative exemplary motion compensation accuracy assessment approach.
Figure 8:
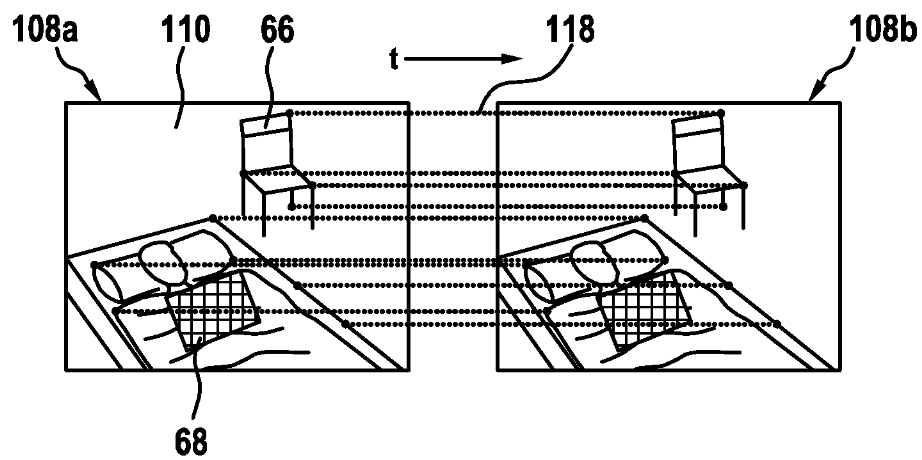
FIG. 8 illustrates yet another alternative exemplary motion compensation accuracy assessment approach.

FIGS. 7*a*, 7*b* and FIG. 8 illustrate exemplary approaches to motion compensation accuracy assessment. In FIG. 7*a*, a motion compensated sequence 106 of motion compensated samples 108*a*, 108*b*, 108*c* is shown. Each of the motion compensated samples 108*a*, 108*b*, 108*c* may represent an image frame out of a series of consecutive image frames. In the motion compensated samples 108*a*, 108*b*, 108*c*, a region of interest 68 is present. Typically, the region of interest 68 comprises a representation of an indicative portion 12 of the subject 10 to be monitored. Furthermore, each of the motion compensated samples 108*a*, 108*b*, 108*c* comprises a non-indicative motion region 110 which may basically stand for a portion of the motion compensated samples 108*a*, 108*b*, 108*c* in which no indicative motion is expected. Consequently, initial motion (in non-compensated signal samples) and motion-related artifacts remaining after motion compensation (in the motion compensated samples) can be present in the non-indicative motion region 110. Preferably, the region of interest 68 is disregarded during motion compensation accuracy assessment. As indicated above, it is preferred that the minute characteristic motion pattern attributable to the vital signal of interest is preserved for signal extraction processing. Consequently, motion compensation accuracy assessment preferably is to be based on at least a portion of the non-indicative motion region 110.

FIG. 7*a* and FIG. 7*b* illustrate similar approaches to motion compensation accuracy assessment. Both approaches can make use of a sum of absolute difference algorithm applied to at least a portion of the non-indicative motion region 110. In other words, a currently to-be-assessed motion compensated sample and a reference (motion compensated) sample can be deduced from one another. A remainder, e.g., a difference sample, obtained through this algorithm can be considered indicative of motion compensation accuracy. Again, it is emphasized that the algorithm is merely applied to a region outside of the region of interest 68. In FIG. 7*a*, the sum of absolute difference estimation operation is indicated by reference numerals 112*a*, 112*b*. In FIG. 7*b*, the sum of absolute difference estimation operation is indicated by reference numerals 114*a*, 114*b*. The above difference samples obtained from the algorithm can form a basis upon which the evaluation parameter can be determined.

In FIG. 7*a* a moving algorithm is applied to the motion compensated samples 108*a*, 108*b*, 108*c*. That is, a currently to-be-assessed sample is compared to a preceding reference sample. The distance or gap between the to-be-assessed sample (e.g., 108*b*) and the respective reference sample (e.g., 108*a*) can be predefined and may be basically constant. The to-be-assessed sample and the respective reference sample may be adjacent or adjoining samples in the motion compensated sequence 106. However, it can be also envisaged that the to-be-assessed sample and the respective reference sample are spaced from one another in the motion compensated sequence 106, that is, further samples can be interposed therebetween. The alternative approach illustrated in FIG. 7*b* makes use of a fixed reference sample (here the motion compensated sample 108*a*). Consequently, each of a series of following consecutive motion compensated samples 108*b*, 108*c* can be linked to the same reference sample 108*a*. In this way, computational costs for motion compensation accuracy assessment can be reduced. However, also a combination of the moving reference approach shown in FIG. 7*a* and the fixed reference shown in FIG. 7*b* can be envisaged. In this way, a basically fixed reference sample can be updated (replaced by a new reference sample) periodically.

FIG. 8 illustrates another exemplary approach to motion compensation accuracy assessment. In this embodiment, explicit feature correspondences in a to-be-processed sample (e.g., motion compensated sample 108*b*) and a reference sample (e.g., motion compensated sample 108*a*) can be detected. A number of detected feature correspondences, refer to correspondence lines 118 which have been added in FIG. 8 for illustrative purposes, may form a basis on which the evaluation parameter can be established. As mentioned above, it is preferred that the region of interest 68 is excluded from the detection of the feature correspondences 118. Consequently, features correspondence detection is to be applied to at least a portion of the non-indicative motion region 110. Feature correspondence detection can make use of corner detection, edge detection, blob detection, ridge detection, etc. It goes without saying that also the approach illustrated in FIG. 8 can make use of "moving" reference samples and "fixed" reference samples, refer to FIGS. 7*a* and 7*b*.

Figure 9A:
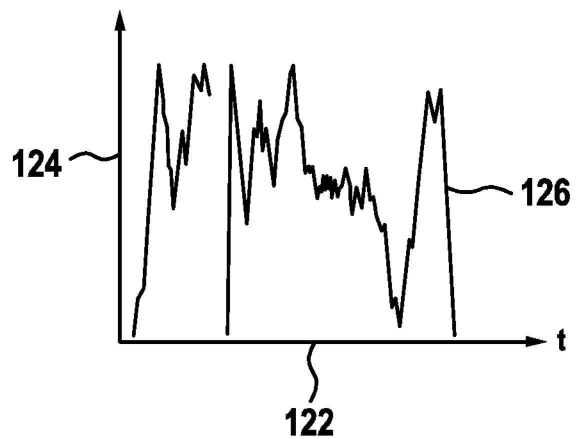
FIG. 9*a* exemplifies an illustration of a characteristic signal obtained from motion corrupted samples.
Figure 9B:
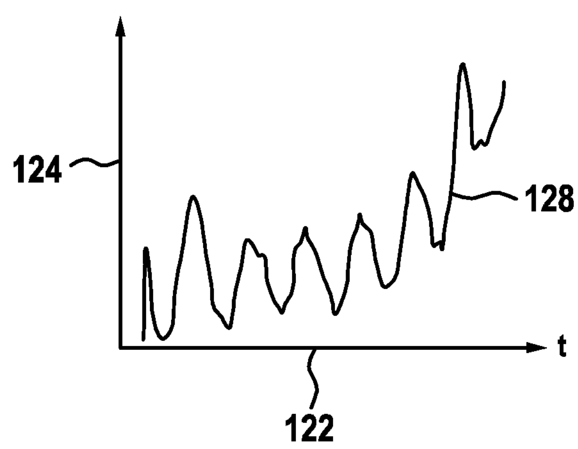
FIG. 9*b* exemplifies an illustration of another characteristic signal obtained from motion compensated samples classified as good samples.

FIG. 9*a* and FIG. 9*b* illustrate several exemplary signal forms 126, 128 obtained through remote vital signal monitoring directed to the detection of a subject's 10 respiration rate (or: breath rate). An axis of abscissas 122 denotes time (or, for instance, sample number, or frame number) while an ordinate axis 124 denotes qualitative or quantitative signal parameters representing detected motion. FIG. 9*a* illustrates a characteristic signal 126 which has been derived from a set of signal samples to which no sufficient motion compensation measures have been applied. Consequently, the characteristic signal 126 is heavily corrupted due to non-indicative motion disturbances. Consequently, applying vital signal extraction measures to the characteristic signal 126 probably results in heavily distorted vital signal forms or values. It is therefore considered beneficial that, in accordance with some embodiments of the present disclosure, signal samples which are assessed and graded as "bad" samples can be excluded from downstream vital signal processing.

By contrast, FIG. 9*b* illustrates a characteristic signal 128 which clearly reflects an underlying at least partially periodic motion pattern which is attributable to indicative motion of the subject 10. The characteristic signal 128 has been derived from a set of motion compensated samples which were graded as "good" samples. Disregarding bad samples in further signal processing may result in a characteristic signal exhibiting an improved signal-to-noise ratio. Based on FIG. 9*b*, for instance, an indicative frequency of recurring extreme values (e.g., minima, maxima, etc.) can be detected which may represent the subject's 10 respiration rate. It should be noted in this connection that the characteristic signal 128 may still comprise disturbances attributable to non-indicative motion. However, exemplarily referring to respiration rate determination, periodic changes in the characteristic signal 128 are clearly visible and can therefore be processed and analyzed so as to derive the desired vital signal of interest.

Figure 10:
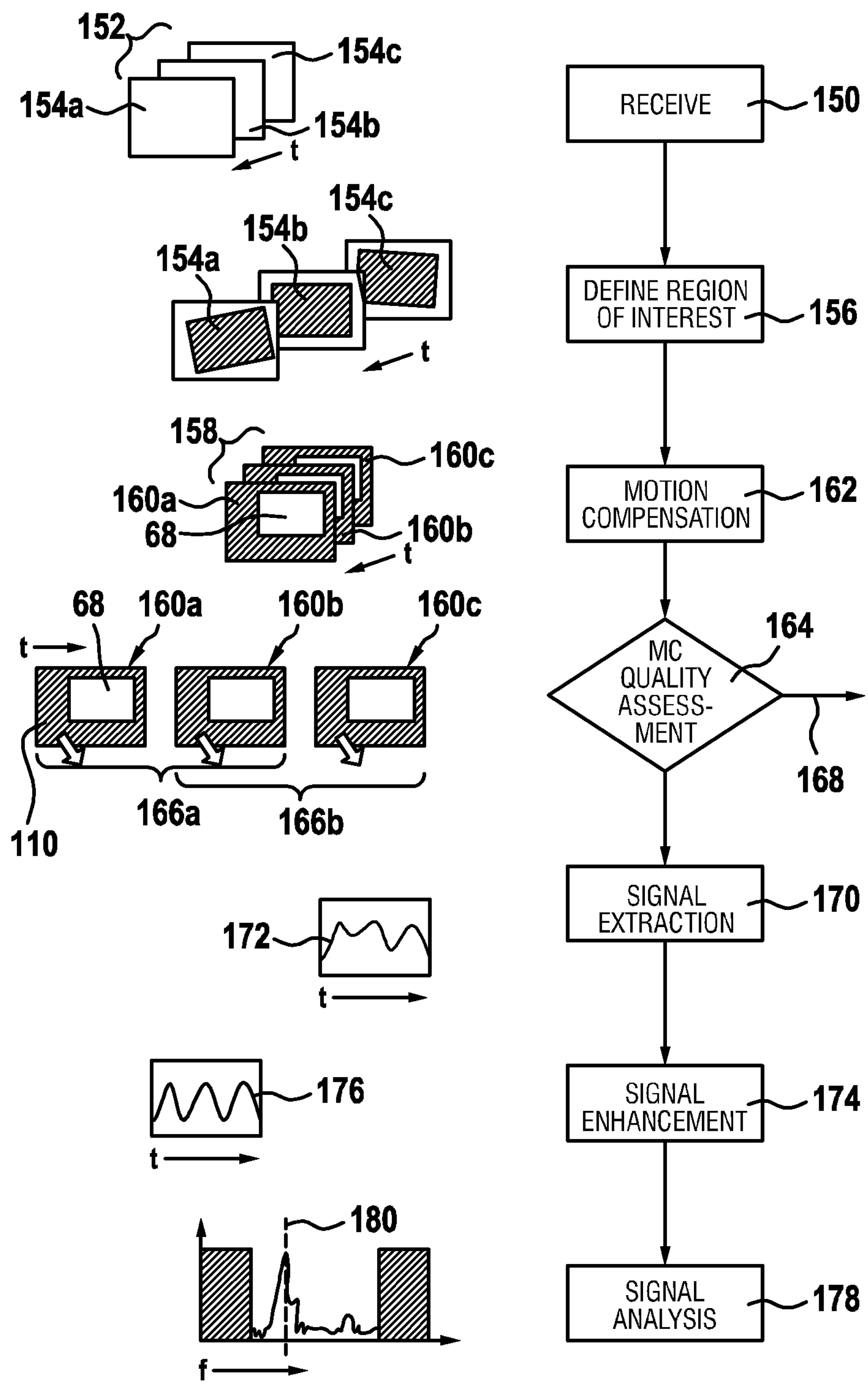
FIG. 10 shows an illustrative block diagram representing several steps of an embodiment of a method according to the disclosure.

Having demonstrated several alternative exemplary approaches covered by the disclosure, FIG. 10 is referred to, schematically illustrating a method for extracting information from remotely detected electromagnetic radiation. Initially, in a step 150, an input data stream comprising a sequence 152 of signal samples 154*a*, 154*b*, 154*c* is received. An arrow t may denote time or an actual frame number. The data stream can be delivered from a sensor means 22 or a data buffer or storage means. The data stream can be embodied by a series of image frames varying over time.

A subsequent step 156 may provide for a determination of a region of interest 68 and, consequently, of a non-indicative motion region 110 in the samples 154*a*, 154*b*, 154*c* of the sequence 152. In a further step 162, concurrently or lagged, motion compensation measures can be applied to the samples 154*a*, 154*b*, 154*c* so as to arrive at a sequence 158 of motion compensated samples 160*a*, 160*b*, 160*c*. For instance, overall motion can be addressed in this way which can be induced by sensor motion, or, specifically, camera motion, in particular with hand-held mobile device applications. It is preferred in this connection that the motion compensation measures are based on motion detection which is basically directed to a non-indicative region 110 in the signal samples 154*a*, 154*b*, 154*c* which is separate from the region of interest 68 which is primarily addressed for extracting the desired vital signals.

A motion compensation quality assessment step 164 may follow. Again, in some embodiments, it is preferred that motion compensation quality assessment is based on at least a portion of the non-indicative motion region 110 in the motion compensated samples 160*a*, 160*b*, 160*c*. Consequently, the region of interest 68 which assumingly exhibits an indicative motion pattern can be disregarded during the motion compensation quality assessment operation. Depending on a detected evaluation parameter 166*a*, 166*b* which may represent a grade of motion compensation quality, the respective to-be-assessed sample can be excluded from or included in further signal processing measures. Motion compensation quality assessment may involve a comparative assessment of a currently to-be-assessed sample 160*b*, 160*c* with respect to a respective reference sample 160*a* and 160*b*, respectively. The motion compensation quality assessment operation 164 may further involve the generation of an output signal 168. The output signal 168 can be directed to a user which can be advised to reduce disturbing motion influences, if required. In this connection, the user can be prompted to keep the device 18 or, at least, the sensor means 22 stable. In addition to the desired indicative motion pattern the subject may have undesired non-indicative body motion (e.g. may be moving his body to the left or right). Similar to camera motion the undesired non-indicative body motion may also cause disturbance for physiological information extraction. The disturbance may be compensated for using the static elements or objects in the background as reference, similar as described above. The output signal 168 directed to the user may provide advice to reduce disturbing motion influences caused by movement of the subject.

Motion compensated samples 160*a*, 160*b*, 160*c* which are graded as "good" samples can form a signal basis from which a characteristic signal 172 can be derived in a signal extraction step 170. Since heavily distorted samples are excluded, the characteristic signal 172 can already be considered highly indicative of the vital signal of interest. However, in some exemplary embodiments, a further signal enhancement operation 174 may follow which may involve, for example, high pass filtering, low pass filtering, bandwidth filtering, windowing, statistical computation measures, etc. Consequently, an enhanced characteristic signal 176 can be computed. In yet another step 178, signal analysis measures can be applied to the enhanced characteristic signal 176 or, in some cases, to the characteristic signal 172. These measures can be directed to seek for particular characteristics indicative of at least one desired vital signal 180. Signal analysis operation 178 may comprise transforming the characteristic signals 172, 176 which are based in the time domain into a transformed signal which is based in the frequency domain.

Needless to say, in an embodiment of a method in accordance with the disclosure, several of the steps provided here can be carried out in changed order, or even concurrently. Further, some of the steps could be skipped as well without departing from the scope of the disclosure. This applies in particular to several alternative signal processing steps.

By way of example, the present disclosure can be applied in the field of healthcare, for instance, unobtrusive remote patient monitoring, general surveillances, securing monitoring and so-called lifestyle environments, such as fitness equipment, or the like. Applications may involve monitoring of respiration rate, respiration rate variability and related vital signals.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for determining at least one vital sign signal, the device comprising:

a camera for receiving a video data stream comprising a sequence of images capturing electromagnetic radiation emitted or reflected by a subject; and a processor configured for processing the sequence of images by operations comprising:

stabilizing the sequence of images including performing a motion compensation operation to derive a sequence of motion compensated images;

assigning each motion compensated image of the sequence of motion compensated images as either a motion compensated image to be kept in the sequence of motion compensated images or a motion compensated image to be excluded from the sequence of motion compensated stabilized images, the motion compensated images to be kept in the sequence of motion compensated images including motion compensated images in which a similarity parameter defined to represent similarity between neighboring motion compensated images or a similarity between each motion compensated image and a reference image exceeds a predefined level, and the motion compensated images to be excluded from the sequence of motion compensated images including motion compensated images in which the similarity parameter defined to represent similarity between neighboring motion compensated images or the similarity between each motion compensated image and the reference image does not exceed the predefined level;

deriving at least one characteristic signal at least partially indicative of an at least partially periodic motion pattern;

determining temporal variations in the at least partially periodic motion pattern of the at least one characteristic signal, the temporal variations being representative of at least one vital sign signal; and determine the at least one vital sign signal from the temporal variations in the at least partially periodic motion pattern of the at least one characteristic signal;

wherein the sequence of images is indicative of desired subject motion and of disturbing motion, the sequence of images capturing at least one region of interest exhibiting the at least partially Periodic motion pattern attributable to at least one physiological parameter, and a non-indicative motion region;

wherein the sequence of motion compensated images are at least partially compensated for undesired overall motion by the motion compensation operation; and wherein the at least partially Periodic motion pattern is derived from each of the motion compensated images to be kept in the sequence while excluding each of the motion compensated images to be excluded from the sequence.

2. The device as claimed in claim 1, wherein the stabilizing includes detecting and tracking features in at least one portion of the non-indicative motion region in the images of the sequence of images.

3. The device as claimed in claim 1, wherein the assigning includes detecting a similarity between the sequence of motion compensated images, wherein the detecting a similarity is performed in at least one portion of the non-indicative motion region in the sequence of motion compensated images.

4. The device as claimed in claim 3, wherein the assigning includes applying an absolute difference processing algorithm to at least one portion of the non-indicative motion region in a respective motion compensated image with respect to a reference image.

5. The device as claimed in claim 1, wherein the assigning includes detecting feature correspondences in at least one portion of the non-indicative motion region in a respective motion compensated image and in a reference image.

6. The device as claimed in claim 1, further comprising a signal generator configured for generating a noticeable output signal indicative of a state of a set of possible states of the at least one characteristic signal, wherein the set of possible states including at least a “good” state and a “bad” state.

7. The device as claimed in claim 1, wherein the camera is configured for capturing electromagnetic radiation within at least one particular wavelength range selected from the group consisting of visible light, infrared light, and ultraviolet radiation, and combinations thereof.

8. A device for determining physiological information, comprising:
- an interface for receiving a data stream derivable from electromagnetic radiation emitted or reflected by a subject; and
- a processor configured for processing the data stream by operations including:
  - deriving a sequence of derivative motion compensated samples from the data stream;
  - detecting an evaluation parameter representative of motion compensation accuracy of the sequence of derivative motion compensated samples; and
  - selectively deriving at least one characteristic signal indicative of an at least partially periodic indicative motion pattern to determine at least one physiological parameter;
- wherein the data stream comprises a sequence of signal samples indicative of desired subject motion attributable to the at least one physiological parameter, and of disturbing motion;
- wherein the derivative motion compensated samples are at least partially compensated for undesired overall motion;
- wherein the at least partially periodic indicative motion pattern is derived from only those derivative motion compensated samples of the sequence of derivative motion compensated samples in which a similarity parameter defined to represent similarity between neighboring derivative motion compensated samples or a similarity between each derivative motion compensated sample and a reference sample exceeds a predefined level, and is not derived from those derivative motion compensated samples in which the similarity parameter defined to represent similarity between neighboring derivative motion compensated samples or the similarity between each derivative motion compensated sample and the reference sample does not exceed the predefined level; and
- wherein deriving the characteristic signal is performed depending on the detected evaluation parameter;
- wherein the device further includes a signal generator configured for generating at least one vital sign signal representative of at least one vital sign from temporal variations in the at least one characteristic signal.

9. A device for determining physiological information, comprising:
- an interface for receiving a data stream derivable from electromagnetic radiation emitted or reflected by a subject; and
- a processor configured for processing the sequence of signal samples by operations; comprising:
  - deriving a sequence of derivative motion compensated samples;
  - detecting an evaluation parameter representative of motion compensation accuracy;
  - deriving at least one characteristic signal at least partially indicative of an at least partially periodic indicative pattern;
  - determining temporal variations in the characteristic signal, the temporal variations being representative of at least one vital sign; and
  - determining the at least one vital sign signal from the temporal variations;
- wherein the data stream comprises a sequence of signal samples including physiological information and indicative of disturbing motion, the sequence of signal samples representing at least one region of interest exhibiting the at least partially periodic indicative pattern attributable to at least one physiological parameter, and a non-indicative motion region;
- wherein the sequence of derivative motion compensated samples are at least partially motion-compensated for undesired overall motion;
- wherein the at least partially periodic indicative pattern is derived from only those derivative motion compensated samples of the sequence of motion compensated samples for which a similarity parameter defined to represent similarity between neighboring derivative motion compensated images or a similarity between each derivative motion compensated image and a reference image exceeds a predefined level, and is not derived from derivative motion-compensated images for which the similarity parameter defined to represent similarity between neighboring derivative motion compensated images or the similarity between each derivative motion compensated image and a reference image does not exceed the predefined level; and
- wherein the deriving of the characteristic signal is performed depending on the detected evaluation parameter;
- wherein the device further includes a signal generator configured for generating an output signal depending on at least one vital sign signal.

10. The device as claimed in claim 9, wherein the signal samples are indicative of desired subject motion and of disturbing motion, the signal samples representing at least one region of interest exhibiting an at least partially periodic indicative motion pattern, the characteristic signal being at least partially indicative of the at least partially periodic indicative motion pattern.

11. A method for determining physiological information, comprising:
- receiving a data stream derivable from electromagnetic radiation emitted or reflected by a subject; and
- processing the data stream, comprising:
  - deriving a sequence of derivative motion compensated samples at least partially compensated for undesired overall motion;
  - detecting an evaluation parameter representative of motion compensation accuracy;

deriving at least one characteristic signal at least partially indicative of an at least partially periodic indicative motion; and determine physiological information from the at least one characteristic signal;

wherein the data stream comprises a sequence of signal samples indicative of desired subject motion and of disturbing motion, the sequence of signal samples representing at least one region of interest exhibiting an at least partially periodic indicative motion pattern attributable to at least one physiological parameter, and a non-indicative motion region;

wherein the at least partially periodic indicative motion pattern is derived from only those derivative motion compensated samples of the sequence of derivative motion compensated samples for which a similarity parameter defined to represent similarity between neighboring derivative motion compensated samples or a similarity between each derivative motion compensated sample and a reference sample exceeds a predefined level, and is not derived from those derivative motion compensated samples for which the similarity parameter defined to represent similarity between neighboring derivative motion compensated samples or the similarity between each derivative motion compensated sample and the reference sample does not exceed the predefined level; and wherein the deriving of the characteristic signal is performed depending on the detected evaluation parameter.

12. A computer readable non-transitory medium having instructions stored thereon which, when carried out on a computer, cause the computer to perform the method as claimed in claim 11.

13. A method for determining physiological information, comprising:

receiving a data stream derivable from electromagnetic radiation emitted or reflected by a subject, the data stream comprising a sequence of signal samples comprising physiological information and indicative of disturbing motion, the signal samples representing at least one region of interest exhibiting an at least partially periodic indicative pattern attributable to at least one physiological parameter, and a non-indicative motion region; and processing the sequence of signal samples, comprising:

deriving a sequence of derivative motion compensated samples at least partially compensated for undesired overall motion from the sequence of signal samples;

detecting an evaluation parameter representative of motion compensation accuracy;

deriving at least one characteristic signal at least partially indicative of the at least partially periodic indicative pattern from the sequence of derivative motion compensated samples, wherein deriving the characteristic signal is performed depending on the detected evaluation parameter, and is performed only on those derivative motion compensated samples in which a similarity parameter defined to represent similarity between neighboring derivative motion compensated samples or a similarity between each derivative motion compensated sample and a reference sample exceeds a predefined level, and is not performed on those derivative motion compensated samples in which the similarity parameter defined to represent similarity between neighboring derivative motion compensated samples or the similarity between each derivative motion compensated sample and the reference sample does not exceed the predefined level; and generating an output signal indicative of physiological information derived from the at least one characteristic signal.

14. A computer readable non-transitory medium having instructions stored thereon which, when carried out on a computer, cause the computer to perform the method as claimed in claim 13.

* * * * *